(12) United States Patent
Kobayashi

(10) Patent No.: US 8,155,269 B2
(45) Date of Patent: Apr. 10, 2012

(54) X-RAY IMAGING APPARATUS

(75) Inventor: Kensuke Kobayashi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 211 days.

(21) Appl. No.: 12/579,283

(22) Filed: Oct. 14, 2009

(65) Prior Publication Data

US 2010/0098213 A1   Apr. 22, 2010

(30) Foreign Application Priority Data

Oct. 16, 2008 (JP) .................................. 2008-267493

(51) Int. Cl.
  *A61B 6/08* (2006.01)
  *G01N 23/083* (2006.01)
  *H05G 1/26* (2006.01)
(52) U.S. Cl. ........... 378/62; 378/164; 378/204; 378/206
(58) Field of Classification Search .................... 378/51, 378/56, 62, 98.8, 162, 164, 189, 197, 198, 378/204–206, 210; 250/559.29, 559.3, 559.31, 250/559.37, 559.38
See application file for complete search history.

(56) References Cited

U.S. PATENT DOCUMENTS

| | | | |
|---|---|---|---|
| 5,714,763 A * | 2/1998 | Chase et al. | 250/559.3 |
| 2003/0194056 A1 | 10/2003 | Spahn | |
| 2004/0105526 A1* | 6/2004 | Zhang et al. | 378/205 |
| 2006/0109958 A1* | 5/2006 | Ertel et al. | 378/205 |
| 2010/0189226 A1* | 7/2010 | Kotowski et al. | 378/198 |

FOREIGN PATENT DOCUMENTS

| | | |
|---|---|---|
| JP | 9-185140 A | 7/1997 |
| JP | 2003-310591 A | 11/2003 |
| JP | 2006-305105 A | 11/2006 |

* cited by examiner

*Primary Examiner* — Anastasia Midkiff
(74) *Attorney, Agent, or Firm* — Canon U.S.A., Inc. IP Division

(57) ABSTRACT

An X-ray imaging apparatus includes an X-ray generation unit configured to irradiate an object with X-rays in a rectangular shape, and an imaging unit which has a rectangular imaging plane and is configured to receive the X-rays transmitted through the object as an X-ray image, wherein the imaging unit is arranged on a plane which is spaced a predetermined distance apart from the X-ray generation unit and perpendicular to an X-ray reference axis such that a center of an irradiation field and a center of the imaging plane match with each other and rotational angles of the irradiation field and the imaging plane around the X-ray reference axis match with each other, by matching at least three visible light beams which have directionality and are irradiated from the X-ray generation unit, with distance indexes provided in the imaging unit.

6 Claims, 10 Drawing Sheets

X-RAY IMAGING APPARATUS

BACKGROUND OF THE INVENTION

1. Field of the Invention

The present invention relates to an X-ray imaging apparatus capable of positioning a device to irradiate an object with X-rays and imaging the object.

2. Description of the Related Art

Generally in X-ray photography, an X-ray generation unit and an imaging unit for receiving X-rays transmitted through an object as an X-ray image are arranged facing each other with the object interposed therebetween. In this case, a distance between the X-ray generation unit and the imaging unit is changed according to an attribute of the object and an imaging site, and respective centers of an X-ray irradiation field and an imaging plane are required to match with each other to prevent grid cut-off.

Examples of a method for recognizing a relative position between the X-ray generation unit and the imaging unit include irradiating a front surface of an imaging unit with visible light, as discussed in Japanese Patent Application Laid-Open No. 2006-305105, irradiating a front surface of an imaging unit, on which an X-ray non-transparent mark is arranged, with X-rays, as discussed in Japanese Patent Application Laid-Open No. 9-185140, and optically recognizing a marker arranged in an imaging unit, as discussed in Japanese Patent Application Laid-Open No. 2003-310591.

In positioning of the X-ray generation unit and the imaging unit, the imaging plane is required to be set right in front of an X-ray emitting plane in addition to carrying out distance adjustment and alignment of centers therebetween. This is because X-rays need to be incident on the imaging plane at right angles to prevent uneven irradiation.

In a general imaging room, a stationary X-ray generation unit of an overhead traveling type or the like and a stationary imaging unit which is fixed to a rack at a standing position or a lie position are installed in many cases. A portable imaging unit is also fixed to the rack when it is used for imaging.

Positioning under such an environment can be easily performed using a suspension unit or a guide of a stand whose vertical and horizontal directions are previously defined. In other words, a large-scale mechanical apparatus is required when the X-ray generation unit and the imaging unit are arranged at suitable relative positions.

Recent series of natural disasters around the world have indicated the importance of prompt diagnosis at the site. What is demanded now is an improvement in the convenience of carriage of and imaging by an X-ray imaging apparatus. This requires that the X-ray generation unit and the imaging unit can be positioned without requiring a large-scale mechanical apparatus.

SUMMARY OF THE INVENTION

The present invention is directed to an X-ray imaging apparatus capable of positioning an X-ray generation unit and an imaging unit without requiring a large-scale mechanical apparatus or the like.

According to an aspect of the present invention, an X-ray imaging apparatus includes an X-ray generation unit configured to irradiate an object with X-rays in a rectangular shape, and an imaging unit which has a rectangular imaging plane and is configured to receive the X-rays transmitted through the object as an X-ray image, wherein the imaging unit is arranged on a plane which is spaced a predetermined distance apart from the X-ray generation unit and perpendicular to an X-ray reference axis such that a center of an irradiation field and a center of the imaging plane match with each other and rotational angles of the irradiation field and the imaging plane around the X-ray reference axis match with each other, by matching at least three visible light beams which have directionality and are irradiated from the X-ray generation unit, with distance indexes provided in the imaging unit.

Further features and aspects of the present invention will become apparent from the following detailed description of exemplary embodiments with reference to the attached drawings, in which like reference characters designate the same or similar parts throughout the figures thereof.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
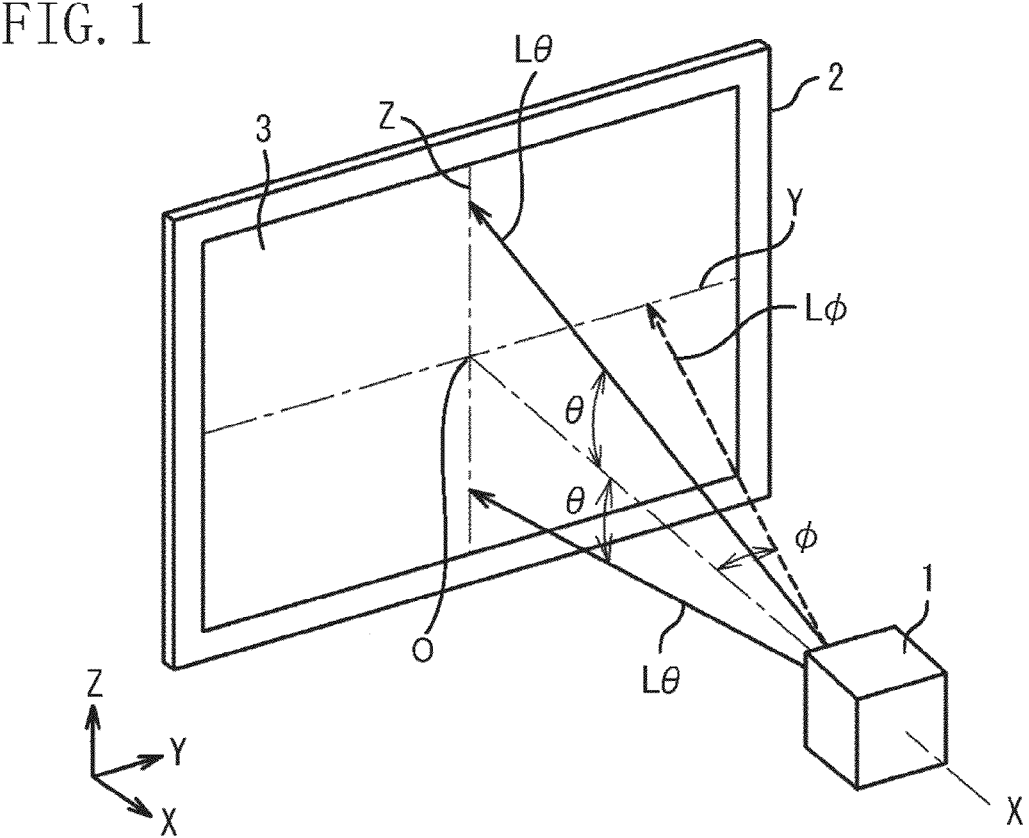
FIG. 1 illustrates positioning in a first exemplary embodiment.

FIG. 1 illustrates positioning of an X-ray generation unit 1 and an imaging unit 2 in a first exemplary embodiment. Three visible light beams which have directionality are irradiated toward an imaging plane 3 of the imaging unit 2 from the X-ray generation unit 1. The two visible light beams L$\theta$ travel upward and downward at a deflection angle $\theta$ relative to an X-ray reference axis X on a vertical plane (a Z-Y plane) including the X-ray reference axis X, and the other visible light beam L$\phi$ travels at a deflection angle $\phi$ relative to the X-ray reference axis X on a horizontal plane (an X-Y plane).

Figure 2:
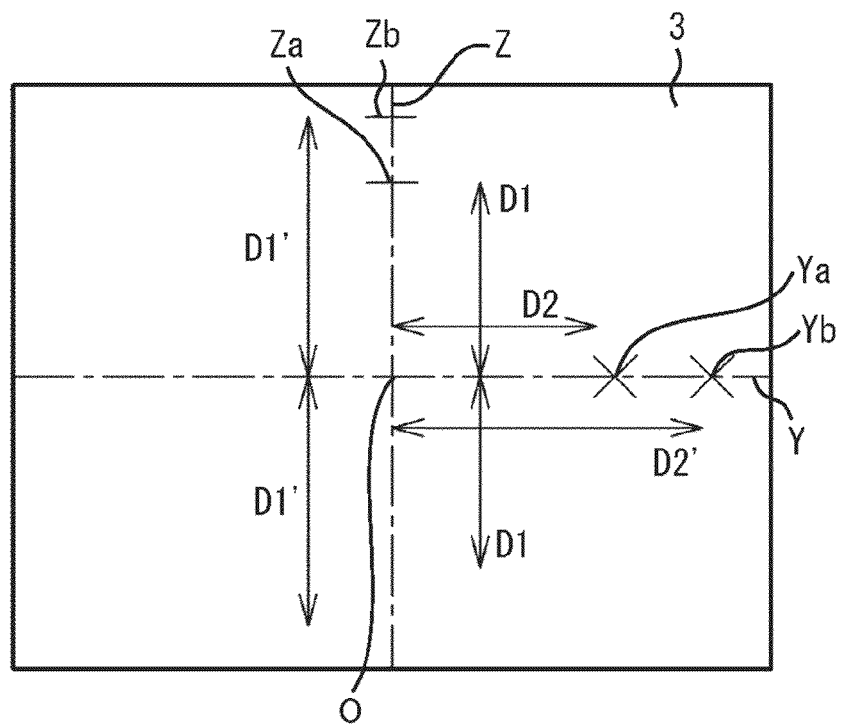
FIG. 2 illustrates an imaging plane in the first exemplary embodiment.

As illustrated in FIG. 2, two types of indexes in a vertical direction and a horizontal direction are provided on the rectangular imaging plane 3 of the imaging unit 2. More specifically, distance indexes Za and Zb, and Ya and Yb, each representing a predetermined distance, are respectively provided on reference axes Z and Y perpendicular to each other. Although in the present exemplary embodiment, two types of distance indexes are used, three or more types of distance indexes may be used.

Figure 3:
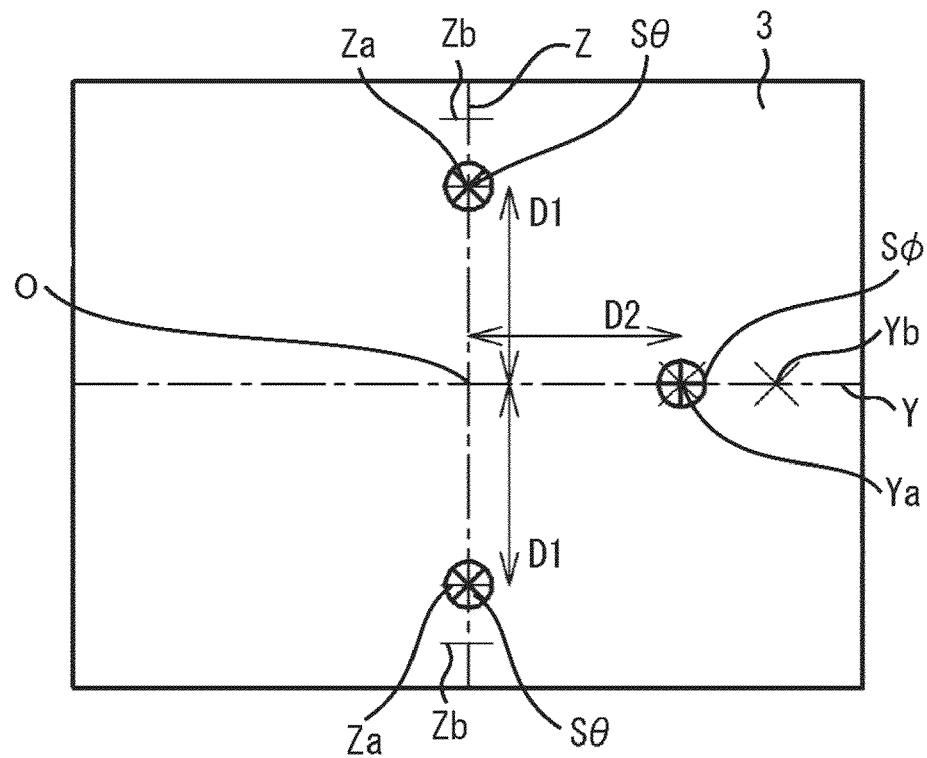
FIG. 3 illustrates positioning on the imaging plane in the first exemplary embodiment.

When the imaging plane 3 spaced a distance D apart from the X-ray generation unit 1 is right in front of an X-ray emitting plane of the X-ray generation unit 1, and their respective centers match with each other, two spots S$\theta$ and one spot S$\phi$ of the visible light beams L$\theta$ and L$\phi$ respectively match with the distance indexes Za and Ya, as illustrated in FIG. 3. More specifically, the visible light beams L$\theta$ are deflected upward and downward at the same angle $\theta$ relative to the X-ray reference axis X. Distances D1 from the spots S$\theta$ in the vertical direction to a center index O in an imaging range are expressed as D1=D·tan $\theta$. On the other hand, a distance D2 from the spot S$\phi$ in the horizontal direction to the center index O is expressed as D2=D·tan $\phi$.

The distances D1 and D2 change according to the distance D from the X-ray generation unit 1. If the positioning is performed at a distance longer than the distance D, therefore, the visible light spots S$\theta$ and S$\phi$ may respectively match with the distance indexes Zb and Yb at distances D1' and D2' from the center index O.

Therefore, the X-ray generation unit 1 need not be provided with a mechanism for adjusting the deflection angles of the visible light beams L$\theta$ and L$\phi$. Moreover, the positioning can be easily completed without moving the X-ray generation unit 1 and the imaging unit 2. The present exemplary embodiment illustrates only three points which are minimum required to define a plane. Pieces of equipment for the X-ray generation unit 1 can be minimized.

Figure 4:
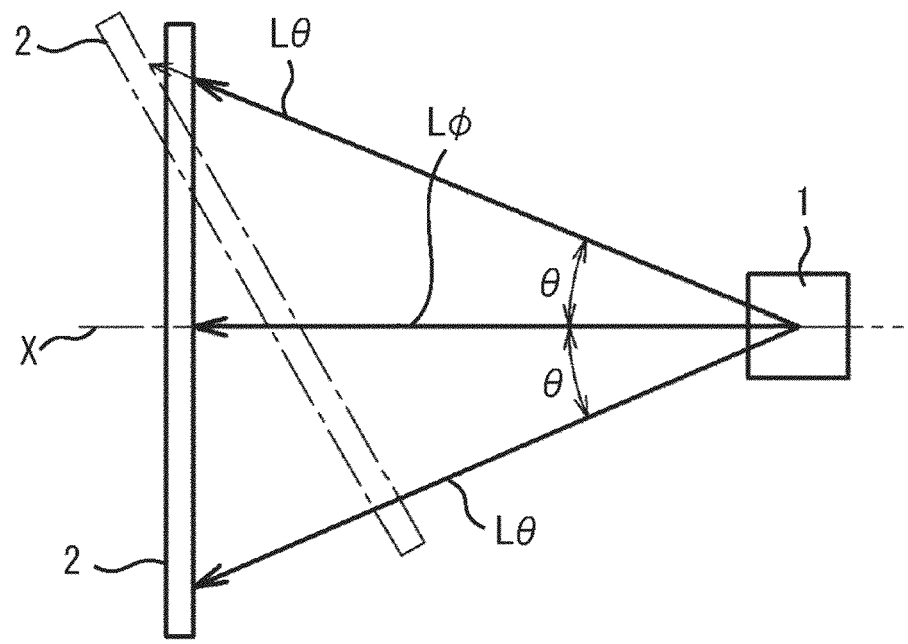
FIG. 4 illustrates a state where an imaging unit is inclined in the first exemplary embodiment.

In the present exemplary embodiment, even when the imaging unit 2 is not at an original position, as indicated by a broken line in FIG. 4, the spot S$\theta$ of the visible light beam L$\theta$ in the vertical direction (Z direction) may, in some cases, match with the distance index Za in the vertical direction. However, the spot S$\phi$ of the visible light beam L$\phi$ in the horizontal direction (Y direction) deviates from the distance index Ya in the horizontal direction. Therefore, it can be easily visually recognized whether the imaging unit 2 and the X-ray generation unit 1 are right in front of each other.

In the present exemplary embodiment, when the vertical direction and the horizontal direction are replaced with each other, the distance indexes Ya and Yb in the horizontal direction may be respectively moved or copied to positions line-symmetric to the indexes Za and Zb in the vertical direction.

Figure 5:
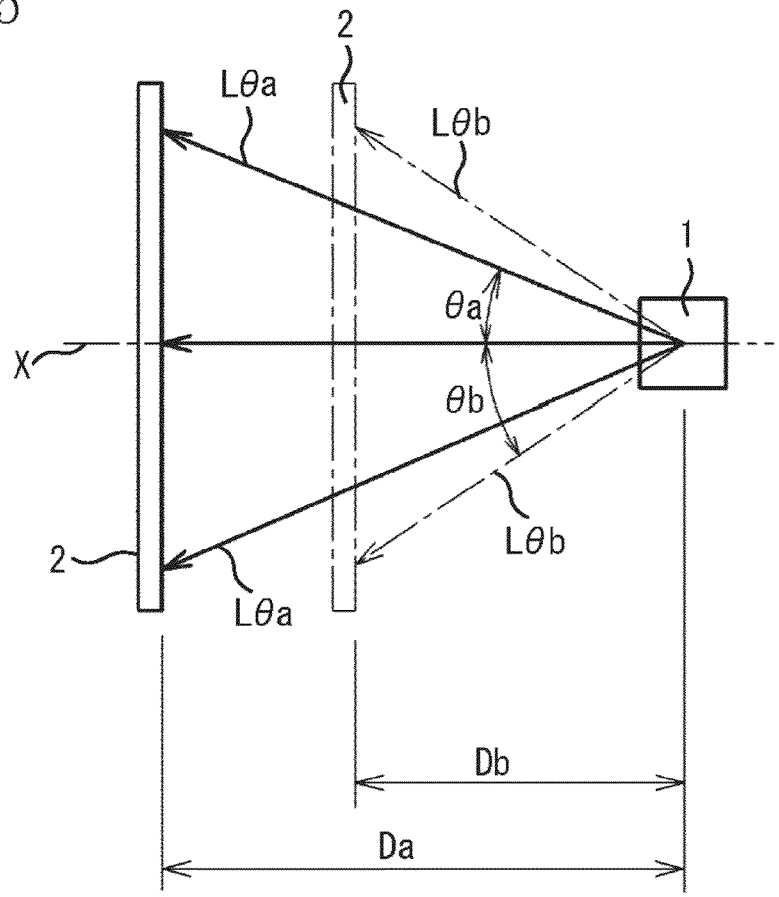
FIG. 5 illustrates a state where a distance between an X-ray generation unit and an imaging unit changes in a second exemplary embodiment.
Figure 6:
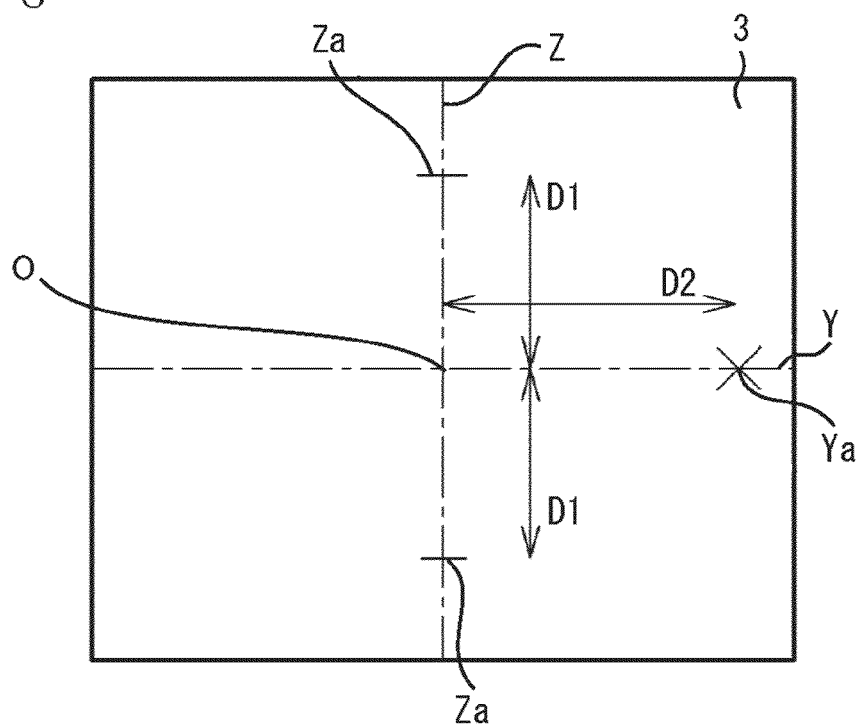
FIG. 6 illustrates an imaging plane in the second exemplary embodiment.

FIG. 5 illustrates positioning in a second exemplary embodiment. It is assumed that both deflection angles $\theta$ and $\phi$ of visible light beams L$\theta$ and L$\phi$ can vary according to a distance. The present exemplary embodiment can be realized even if only one type of distance index is provided to each in the vertical direction and the horizontal direction on an imaging plane 3, as illustrated in FIG. 6. More specifically, when the distance between the X-ray generation unit 1 and the imaging plane 3 is defined as Da to the visible light beam L$\theta$a which is deflected by the angle $\theta$a, respective distances D1 and D2 from a center index O to distance indexes Za and Ya are defined by the following equation.

$$D1 = Da \cdot \tan \theta a$$

If the distances D1 and D2 are defined using the same indexes when the distance is Db, the deflection angle of the visible light beam L$\theta$b may be changed to an angle $\theta$b that satisfies the following equation.

$$D1 = Db \cdot \tan \theta b$$

The same is true for a visible light beam L$\phi$b.

As described above, even when a plurality of distance indexes is not previously provided on each of the reference axes Z and Y on the imaging plane 3, the positioning can be easily accomplished. More specifically, if the deflection angles of the visible light beams L$\theta$ and L$\phi$ are accurately adjusted, the positioning can be accomplished by respectively matching visible light spots with the distance indexes Za and Ya on the imaging plane 3. This can prevent a wrong choice from among a plurality of indexes.

Further, when the deflection angles of the visible light beams L$\theta$ and L$\phi$ are determined such that the visible light spots match with an external shape of an irradiation range, an irradiation field can be confirmed simultaneously with the positioning.

Figure 7:
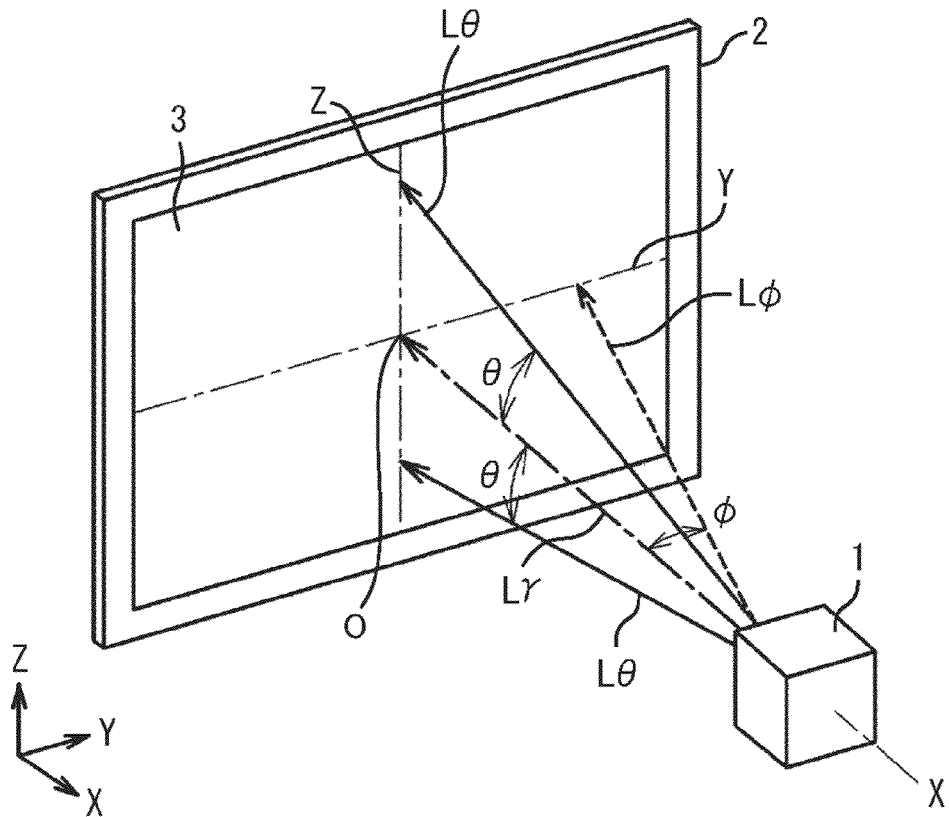
FIG. 7 illustrates positioning in a third exemplary embodiment.

FIG. 7 illustrates positioning in a third exemplary embodiment. Four visible light beams are irradiated from an X-ray generation unit 1. The one visible light beam L$\gamma$ match with an X-ray reference axis X. The one set of two visible light beams L$\theta$ defines a vertical plane (a Z-Y plane) including the X-ray reference axis X, and the other one visible light beam L$\phi$ travels on a horizontal plane (an X-Y plane) without matching with the X-ray reference axis X.

Figure 8:
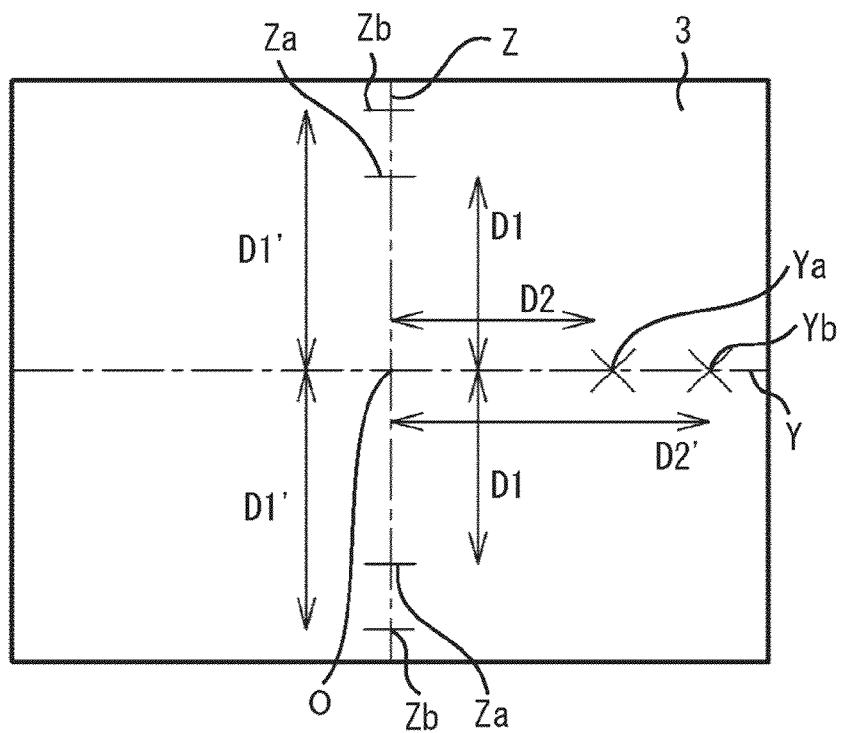
FIG. 8 illustrates an imaging plane in the third exemplary embodiment.

As illustrated in FIG. 8, on an imaging plane 3 of an imaging unit 2, there are provided reference axes Z and Y, a center index O of the imaging plane 3 on the planes, and distance indexes Za, Zb, Ya, and Yb, each representing a predetermined distance on the reference axes Z and Y. The distance indexes may be of two or more types.

Figure 9:
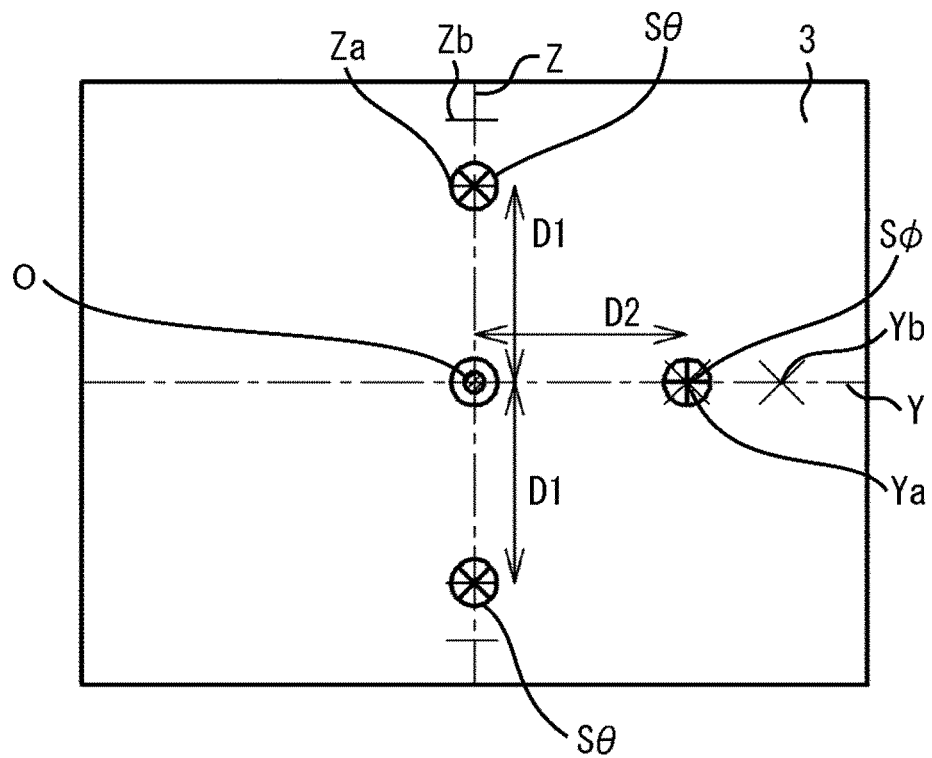
FIG. 9 illustrates positioning on the imaging plane in the third exemplary embodiment.

When the imaging plane 3 spaced a distance D apart from the X-ray generation unit 1 is right in front of an X-ray emitting plane, and their centers match with each other, spots S$\theta$ and S$\phi$ of the visible light beams respectively match with the distance indexes Za and Ya, as illustrated in FIG. 9. The visible light beams L$\theta$ are deflected upward and downward at the same angle $\theta$ relative to the X-ray reference axis X. Therefore, distances D1 between the spot S$\theta$ in the vertical direction and the center index O are expressed as D1=D·tan $\theta$. On the other hand, a distance D2 between the spot S$\phi$ in the horizontal direction and the center index O is expressed as D2=D·tan $\theta$.

The distances D1 and D2 change according to the distance D between the X-ray generation unit 1 and the imaging plane 3. If the positioning is performed at a distance longer than the distance D, therefore, the visible light spots S$\theta$ and ST may respectively match with the distance indexes Zb and Yb.

Therefore, the X-ray generation unit 1 need not be provided with a mechanism for adjusting the deflection angles of the visible light beams. Moreover, the positioning can be easily completed without moving the X-ray generation unit 1 and the imaging unit 2. Furthermore, in the present exemplary embodiment, it can be directly confirmed whether the X-ray reference axis X matches with the center index O in an imaging range, and ease of the positioning can be enhanced.

Figure 10:
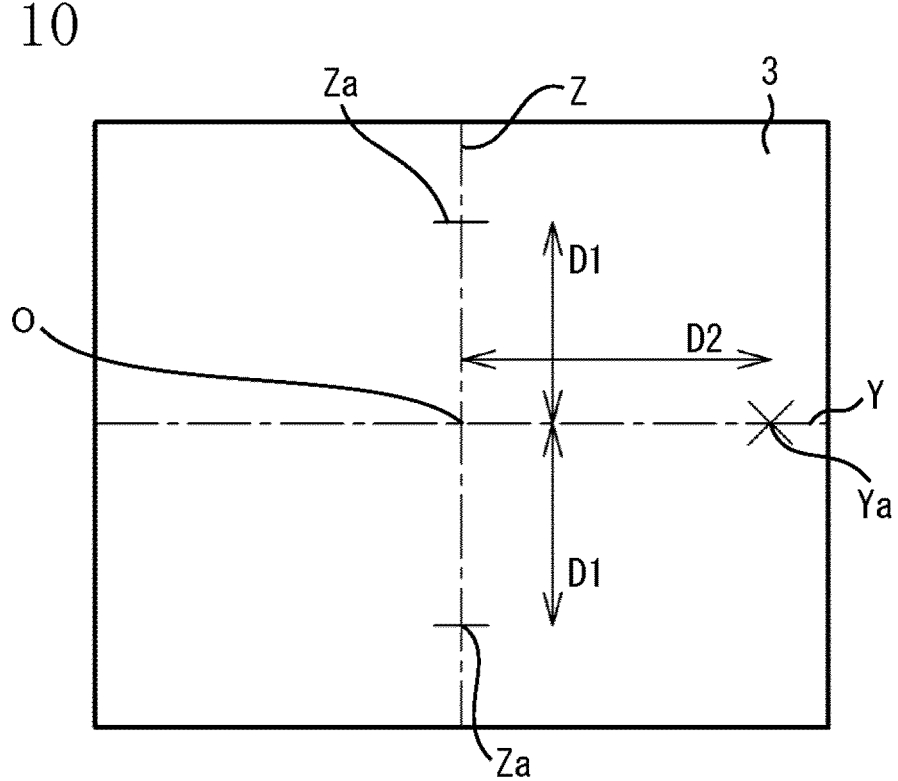
FIG. 10 illustrates an imaging plane in a fourth exemplary embodiment.

FIG. 10 illustrates positioning in a fourth exemplary embodiment. It is assumed that both deflection angles θ and φ of visible light beams Lθ and Lφ can vary according to a distance. The present exemplary embodiment can be realized even if only one type of distance index is provided to each in the vertical direction and the horizontal direction on an imaging plane 3. More specifically, when the distance between the X-ray generation unit 1 and the imaging plane 3 is defined as Da to the visible light beam Lθa which is deflected by the angle θa, a distance D1 from a center index O to distance indexes Za is defined by the following equation.

$$D1 = Da \cdot \tan \theta a$$

If the distances D1 and D2 are defined using the same indexes when the distance is Db, the deflection angle of the visible light beam Lθb may be changed to an angle θb that satisfies the following equation.

$$D1 = Db \cdot \tan \theta b$$

The same is true for a visible light beam Lφb.

If the X-ray generation unit 1 thus has a function of adjusting the deflection angles of the visible light beams, it can be directly confirmed whether an X-ray reference axis X matches with the center index O in an imaging range so that the positioning can be easily accomplished even when a plurality of distance indexes is not provided on the imaging plane 3. More specifically, if the deflection angles of the visible light beams are accurately adjusted, visible light spots may respectively match with the only distance indexes on the imaging plane 3. This can prevent a wrong choice from among a plurality of indexes.

Figure 11:
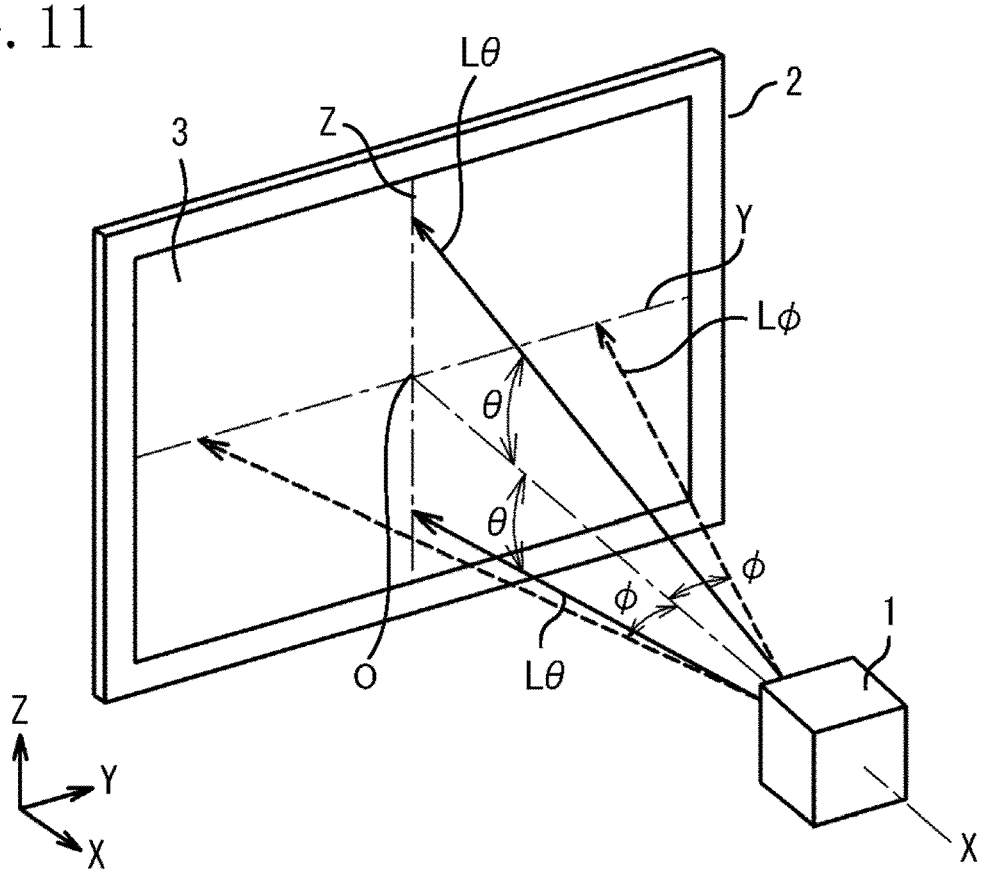
FIG. 11 illustrates positioning in a fifth exemplary embodiment.

FIG. 11 illustrates positioning in a fifth exemplary embodiment. Four visible light beams which have directionality are irradiated from an X-ray generation unit 1. The one set of two visible light beams travels rightward and leftward at a deflection angle θ relative to an X-ray reference axis X on a vertical plane (a Z-Y plane), and the other set of two visible light beams travels upward and downward at a deflection angle φ relative to the X-ray reference axis X on a horizontal plane (an X-Y plane).

Figure 12:
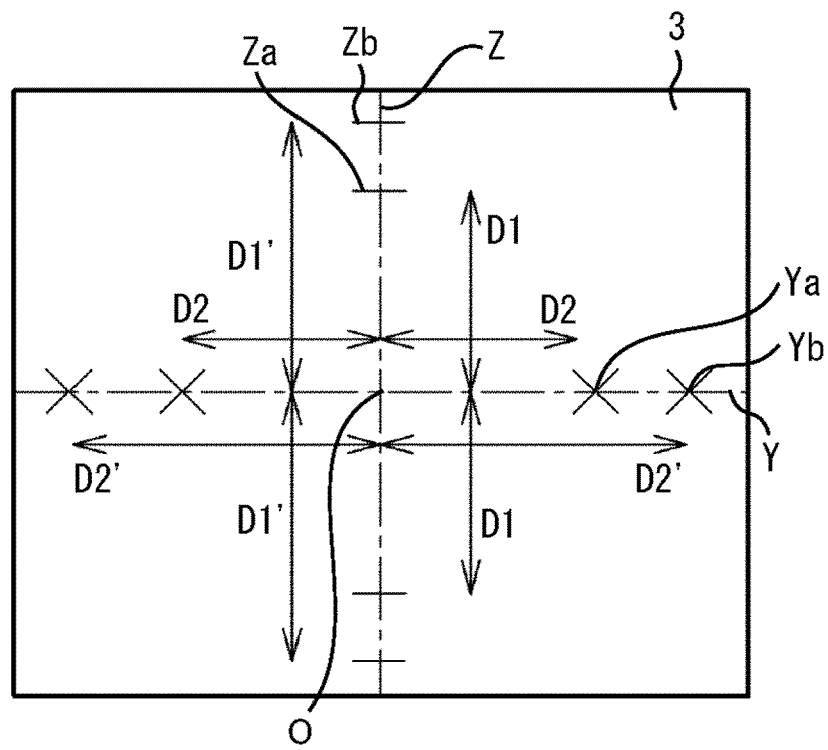
FIG. 12 illustrates an imaging plane in the fifth exemplary embodiment.

As illustrated in FIG. 12, distance indexes Za, Zb, Ya, and Yb are provided on reference axes Z and Y on an imaging plane 3. The distance indexes may be of two or more types.

Figure 13:
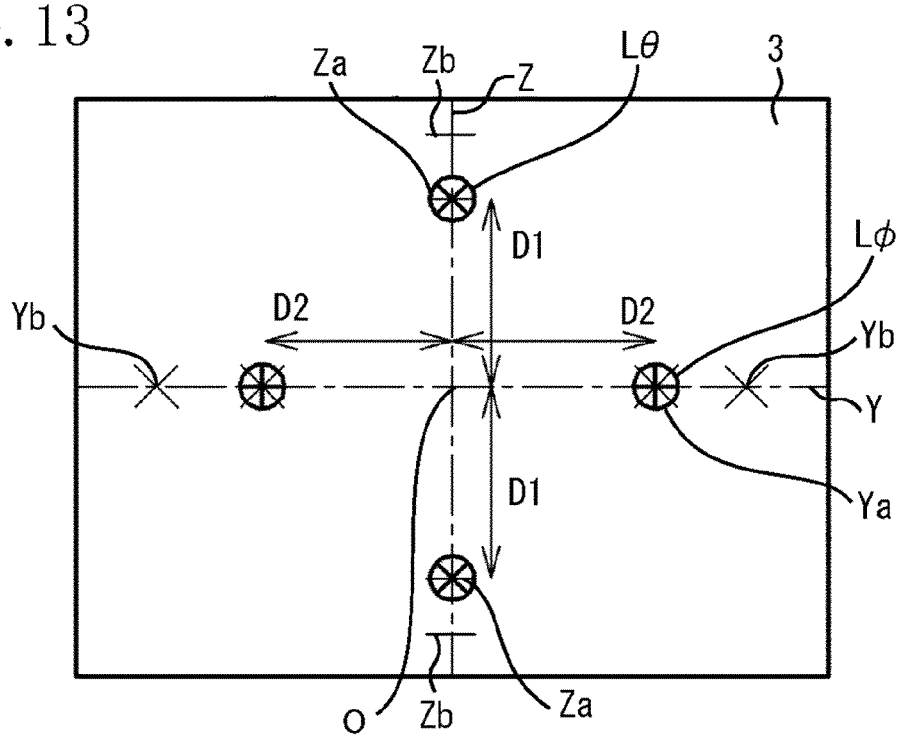
FIG. 13 illustrates positioning on the imaging plane in the fifth exemplary embodiment.

When the imaging plane 3 spaced a distance D apart from the X-ray generation unit 1 is right in front of an X-ray emitting plane, and their centers match with each other, spots Sθ and Sφ of the visible light beams Lθ and Lφ respectively match with the distance indexes Za and Ya, as illustrated in FIG. 13. The visible light beams L in each of the sets are deflected at the same angle θ relative to the X-ray reference axis X. Therefore, distances D1 between the spots Sθ in the vertical direction and a center index O are expressed as $D1 = D \cdot \tan \theta$. On the other hand, distances D2 between the spots Sφ in the horizontal direction and the center index O are expressed $D2 = D \cdot \tan \phi$.

The distances D1 and D2 change according to the distance D from the X-ray generation unit 1. If the positioning is performed at a distance longer than the distance D, therefore, the visible light spots may respectively match with the distance indexes Zb and Yb.

Therefore, the X-ray generation unit 1 need not be provided with a mechanism for adjusting the deflection angles of the visible light beams L. Moreover, the positioning can be easily completed without moving the X-ray generation unit 1 and the imaging plane 3.

Figure 14:
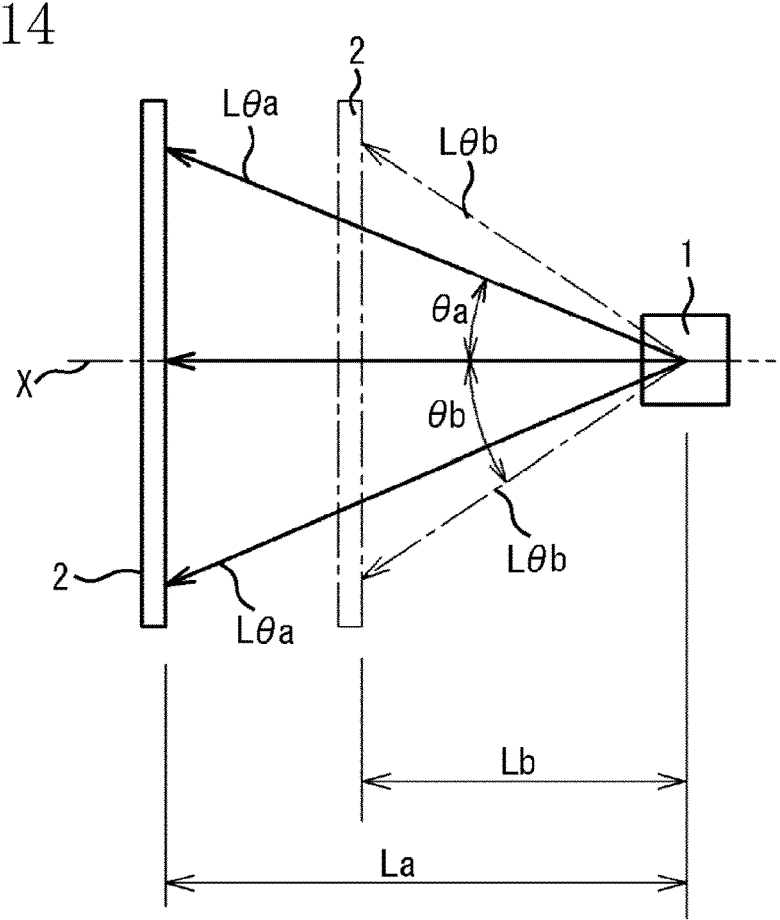
FIG. 14 illustrates a state where a distance between an X-ray generation unit and an imaging unit changes in a sixth exemplary embodiment.
Figure 15:
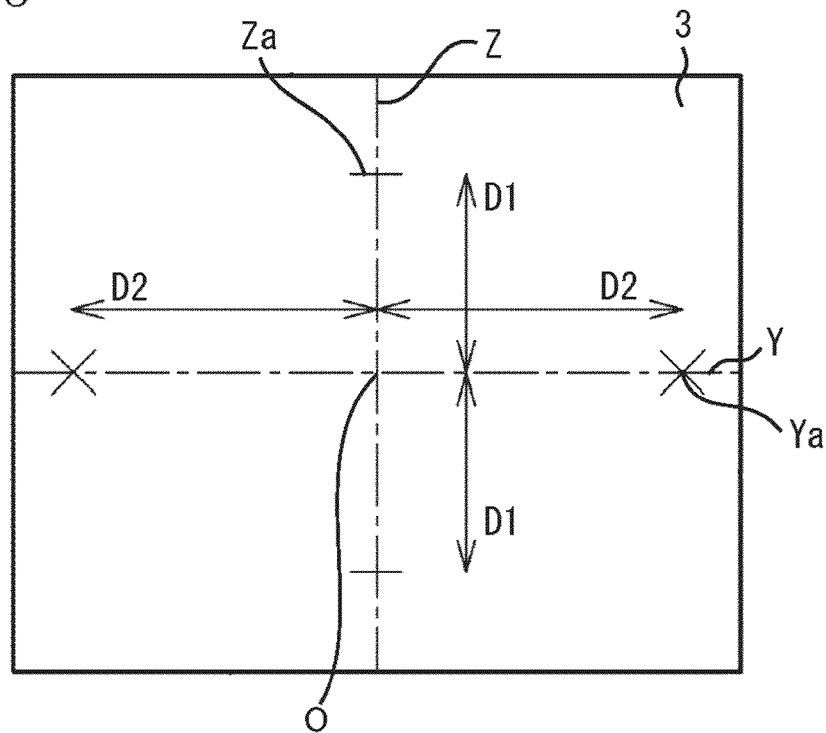
FIG. 15 illustrates an imaging plane in the sixth exemplary embodiment.

FIG. 14 illustrates positioning in a sixth exemplary embodiment. It is assumed that respective deflection angles θ and φ of visible light beams Lθ and Lφ can vary according to a distance. The present exemplary embodiment can be realized even if only one type of distance index is provided to each in the vertical direction and the horizontal direction on an imaging plane 3, as illustrated in FIG. 15.

If an X-ray generation unit 1 has a function of adjusting the deflection angles of the visible light beams L, the positioning can be easily accomplished even when a plurality of distance indexes is not provided on the imaging plane 3. More specifically, if the deflection angles θ and φ of the visible light beams are accurately adjusted, the positioning can be accomplished by matching visible light spots with the only distance indexes Za and Ya on the imaging plane 3. This can prevent a wrong choice from among a plurality of indexes.

Further, when the deflection angles θ and φ of the visible light beams are determined such that the visible light spots match with an external shape of an irradiation range, an irradiation field can be confirmed simultaneously with the positioning.

Figure 16:
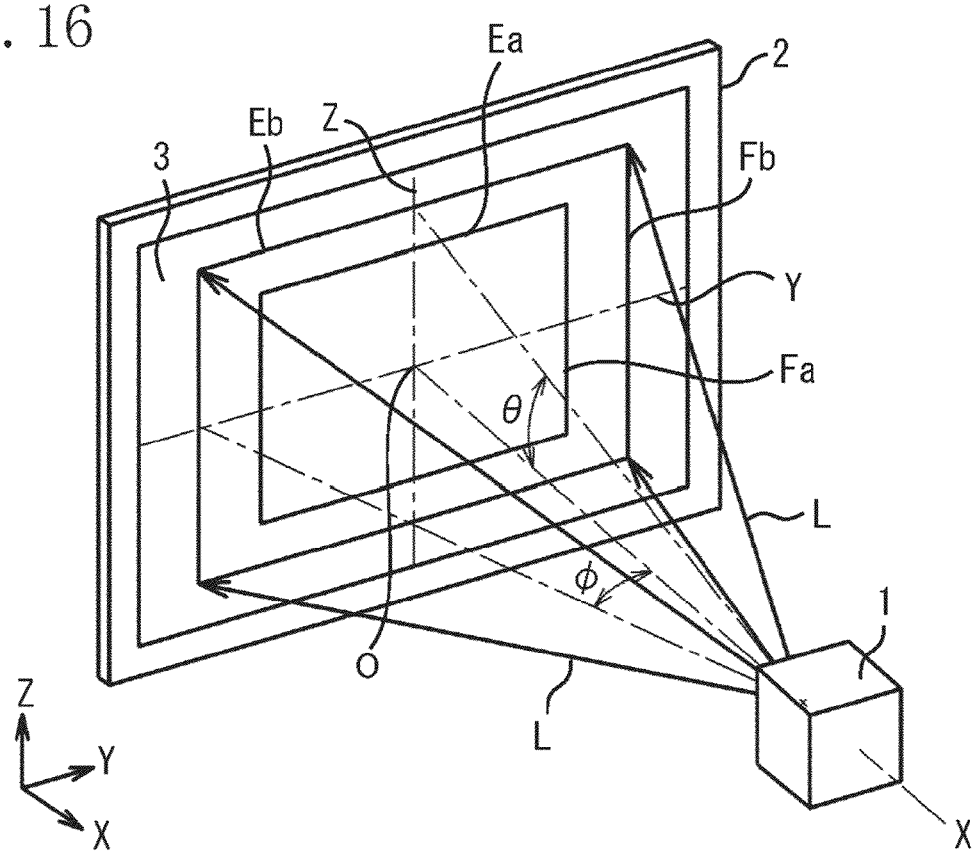
FIG. 16 illustrates positioning in a seventh exemplary embodiment.

FIG. 16 illustrates positioning in a seventh exemplary embodiment. Four visible light beams which have directionality are irradiated from an X-ray generation unit 1. The one set of two visible light beams defines a top side of an irradiation field, and the other set of two visible light beams defines a bottom side of the irradiation field. There exist two sets of two visible light beams that respectively define lateral sides of the irradiation field.

When an imaging unit 2 is spaced a distance D apart from the X-ray generation unit 1, and is right in front of an X-ray emitting plane, each of spots S of the visible light beams L matches with an intersection of a top/bottom side index Eb and a lateral side index Fb on an imaging range. In this case, a distance from a center index O is also a distance index representing the distance D from the X-ray generation unit 1, as in the first exemplary embodiment. Further, the spots S respectively represent vertexes of the irradiation field.

If deflection angles θ and φ of the visible light beams L are fixed, the distances from the center index O to the visible light spots S change according to the distance D from the X-ray generation unit 1. If the positioning is performed at a distance shorter than the distance D, therefore, each of the visible light spots may match with an intersection of side indexes Ea and Fa. Therefore, the X-ray generation unit 1 need not be provided with a mechanism for adjusting the deflection angles of the visible light beams L. Moreover, the positioning can be easily completed without moving the X-ray generation unit 1 and the imaging unit 2.

When all the visible light spots respectively match with the side indexes, the center index O and an X-ray reference axis X match with each other. Therefore, the present exemplary embodiment can be realized even if the center index O in the imaging range does not exist.

Figure 17:
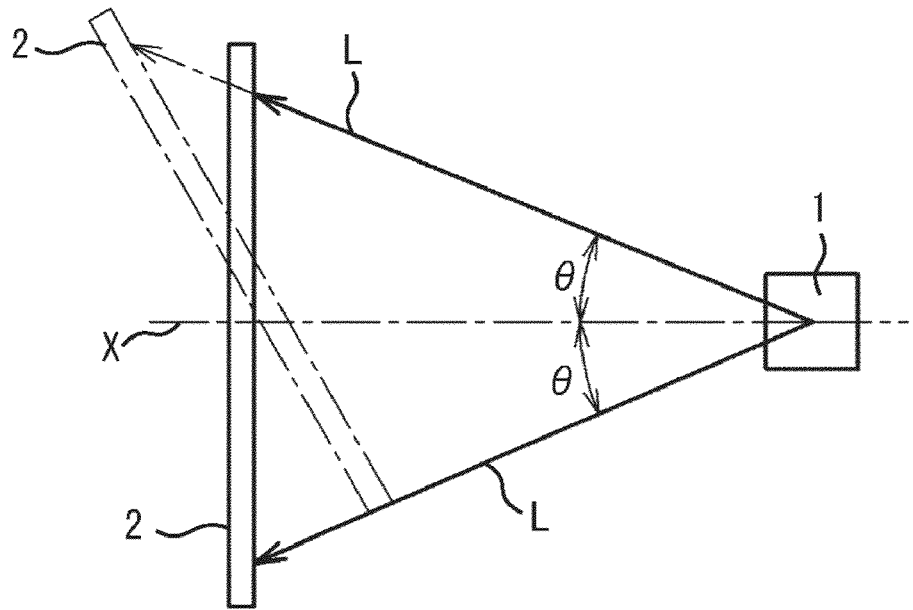
FIG. 17 illustrates a case where an imaging unit is inclined in the seventh exemplary embodiment.
Figure 18:
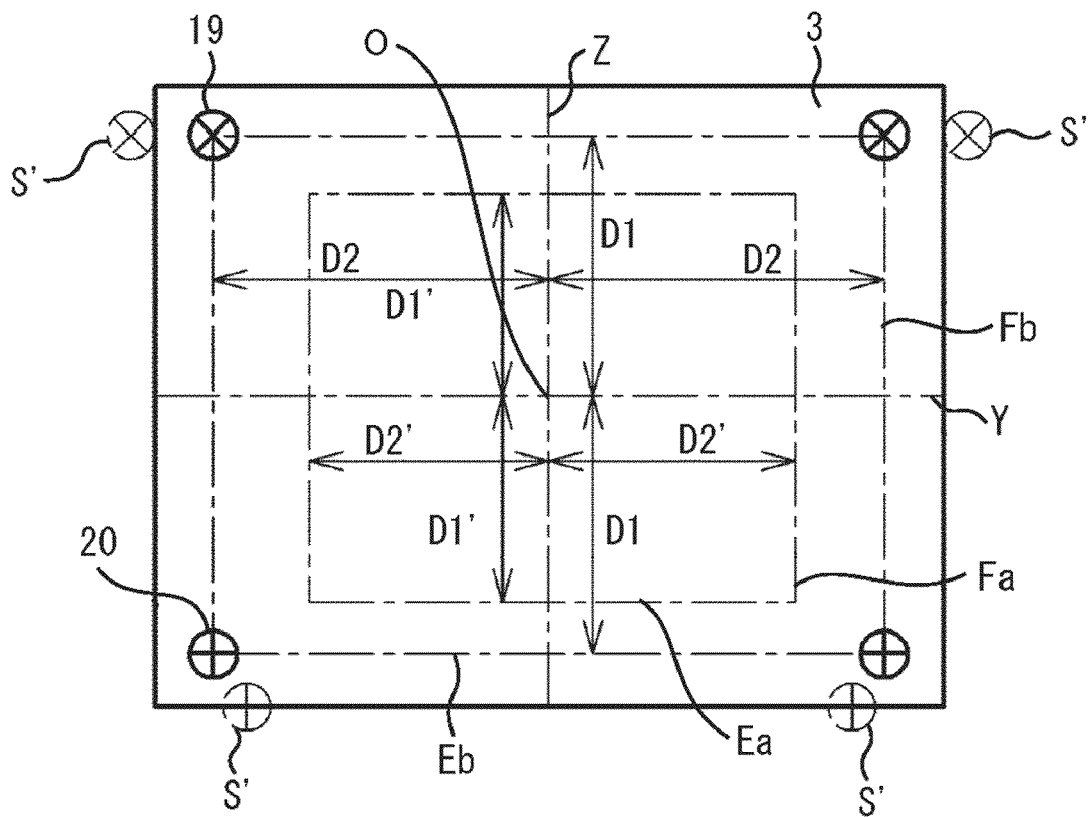
FIG. 18 is a schematic view illustrating positioning on an imaging plane in the seventh exemplary embodiment.

If the visible light beams L are irradiated with the imaging unit 2 which is inclined and shifted in the vertical direction as indicated by a broken line in FIG. 17, visible light spots S' indicated by broken lines in FIG. 18 clearly deviate from the side indexes Eb and Fb. Therefore, it can be easily visually recognized whether the imaging unit 2 and the X-ray generation unit 1 are right in front of each other.

Although in the above-mentioned exemplary embodiment, the visible light beam L matches with a lateral line of a rectangular irradiation range. Therefore, the irradiation field can be visually confirmed simultaneously with the positioning. Thus, a deflection angle adjustment unit and an irradiation field adjustment unit of the visible light beam L can be configured as one unit, and the configuration can be simplified.

Figure 19:
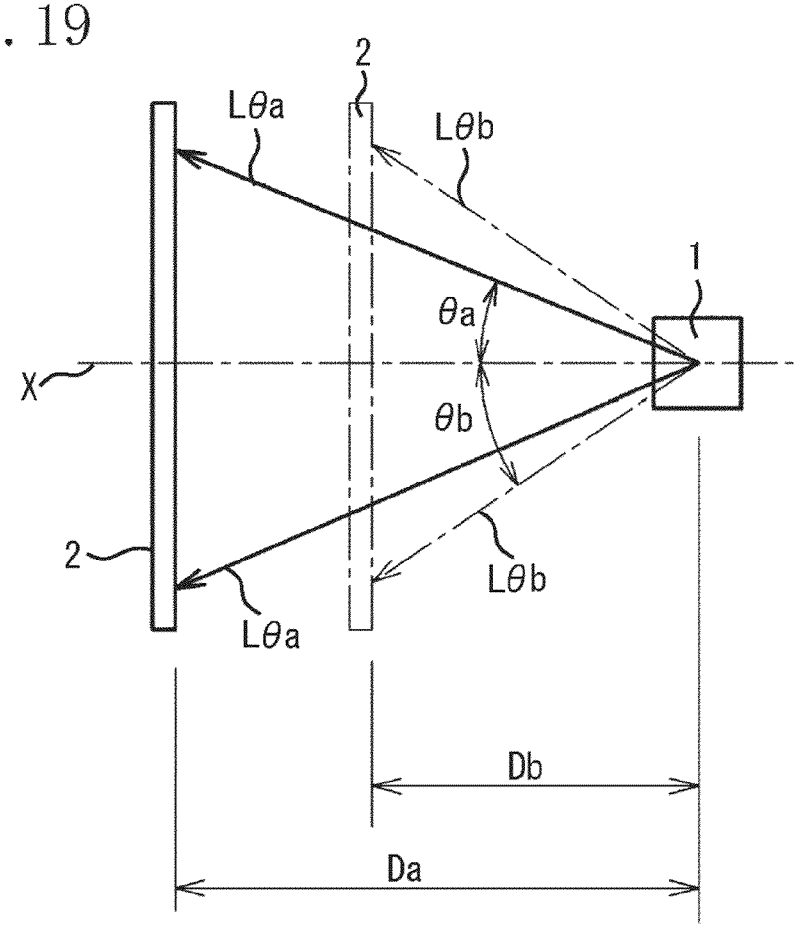
FIG. 19 illustrates a case where an imaging unit is inclined in an eighth exemplary embodiment.
Figure 20:
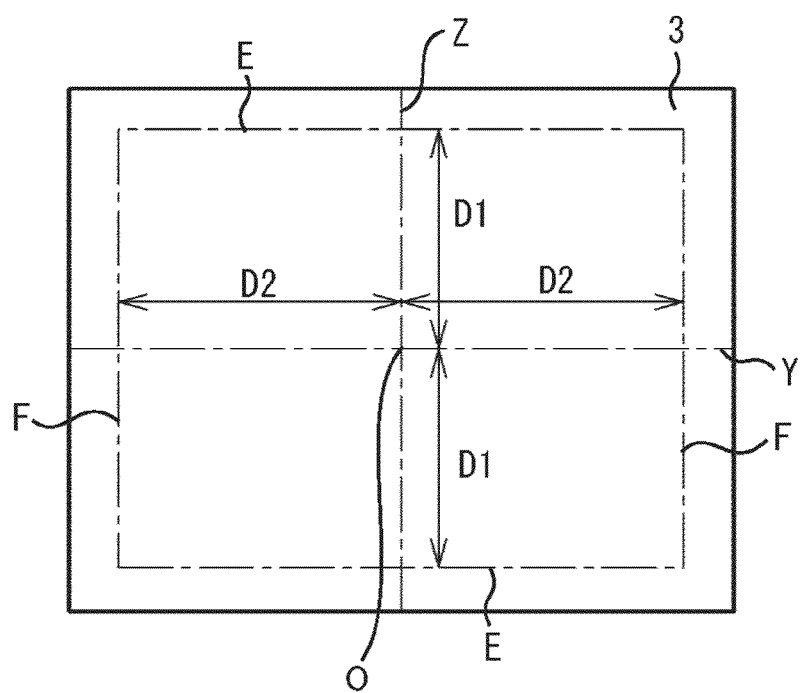
FIG. 20 illustrates an imaging plane in the eighth exemplary embodiment.

FIG. 19 illustrates positioning in an eighth exemplary embodiment. It is assumed that a deflection angle θ of a visible light beam Lθ can vary according to a distance. The present exemplary embodiment can be realized even if only one index is provided to each of top/bottom side index E and lateral side index F on an imaging plane 3, as illustrated in FIG. 20. More specifically, if a distance between an X-ray generation unit 1 and the imaging plane 3 is defined as Da to the visible light beam Lθa which is deflected by the angle θa, a distance D1 from a center index O to the side index E is defined by the following equation.

$$D1 = Da \cdot \tan \theta a$$

If the distance D1 is defined using the same indexes when the distance is Db, however, the deflection angle of the visible light beam Lθb may be changed to an angle θb that satisfies the following equation:

$$D1 = Db \cdot \tan \theta b$$

If the X-ray generation unit 1 thus has a function of adjusting the deflection angles of the visible light beam L, the positioning can be easily accomplished even when no distance index is provided on the imaging plane 3. More specifically, if the deflection angles θ and φ of the visible light beam L are accurately adjusted, the positioning can be accomplished by matching visible light spots with the side indexes E and F on the imaging plane 3. This can prevent a wrong choice from among a plurality of indexes.

Further, the visible light beam L matches with a lateral line of a rectangular irradiation range that can be adjusted by a diaphragm. Therefore, an irradiation field can be visually confirmed simultaneously with the positioning. Thus, a deflection angle adjustment unit and an irradiation field adjustment unit of the visible light beam L can be configured as one unit, and the configuration can be simplified.

As described above, in the X-ray imaging apparatus according to the present invention, the distance between the X-ray generation unit and the imaging unit, the plane of the imaging unit which is right in front of the X-ray emitting plane, and the relative rotational angle to the X-ray reference axis can be simultaneously defined using the directional visible light beams having visibility. Therefore, positioning accuracy can be easily improved.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-267493 filed Oct. 16, 2008, which is hereby incorporated by reference herein in its entirety.

What is claimed is:

1. An X-ray imaging apparatus comprising:
an X-ray generation unit configured to irradiate an object with X-rays in a rectangular shape; and configured to emit a plurality of visible light beams including a visible light beam that matches with an X-ray reference axis, a set of two visible light beams that define a first plane including the X-ray reference axis, and a visible light beam that travels on a second plane without matching with the X-ray reference axis;
an imaging unit which has a rectangular imaging plane and is configured to receive the X-rays transmitted through the object as an X-ray image,
wherein the rectangular imaging plane has a center index at its center thereof where a first reference axis and a second reference axis perpendicular to the first reference axis intersect with each other, and the rectangular imaging plane includes a plurality of distance indexes on the first reference axis and the second reference axis each distance index representing a predetermined distance between the X-ray generation unit and the imaging unit, and
wherein the imaging unit is arranged on an imaging plane which is spaced at each of the predetermined distances represented by the plurality of distance indexes apart from the X-ray generation unit and perpendicular to the X-ray reference axis such that a center of an irradiation field and a center of the imaging plane match with each other and rotational angles of the irradiation field and the imaging plane around the X-ray reference axis match with each other, by matching the plurality of visible light beams with the plurality of distance indexes provided in the imaging unit.

2. The X-ray imaging apparatus according to claim 1, wherein the visible light beam that matches with the X-ray reference axis coincides with the center index, the set of two visible light beams that define the first plane are deflected in opposite directions along the first plane at a first angle relative to the X-ray reference axis, and the visible light beam that travels on the second is deflected along the second plane perpendicular to the first plane at a second angle.

3. The X-ray imaging apparatus according to claim 1, wherein the set of two visible light beams have the same deflection angle relative to the X-ray reference axis on a plane which passes through the X-ray reference axis.

4. The X-ray imaging apparatus according to claim 3, wherein a plane formed by the set of two visible light beams is perpendicular to the second plan.

5. The X-ray imaging apparatus according to claim 2, wherein, in the set of two visible light beams that define the first plane and are deflected in opposite directions along the first plane, the first angle relative to the X-ray reference axis varies according to an imaging range and a distance from the X-ray generation unit to the imaging unit.

6. The X-ray imaging apparatus according to claim 1, wherein the plurality of distance indexes on the first reference axis and the second reference axis includes at least two distance indexes on first reference axis and at least two distance indexes on the second reference axis, and
wherein each distance index on the first reference axis or the second reference axis represents a different distance between the X-ray generation unit and the imaging unit.

* * * * *